(12) United States Patent
Buchanan et al.

(10) Patent No.: US 7,202,276 B2
(45) Date of Patent: Apr. 10, 2007

(54) USE OF 13-HODE AS A REGULATOR OF VASCULAR BIOCOMPATIBILITY AND AN INHIBITOR OF CELL HYPERPLASIA

(75) Inventors: Michael Buchanan, Hamilton (CA); David Horrobin, Bridge of Allan (GB)

(73) Assignee: 1411198 Ontario Limited, Ontario (CA)

( * ) Notice: Subject to any disclaimer, the term of this patent is extended or adjusted under 35 U.S.C. 154(b) by 0 days.

(21) Appl. No.: 09/833,257

(22) Filed: Apr. 9, 2001

(65) Prior Publication Data

US 2002/0028848 A1 Mar. 7, 2002

(30) Foreign Application Priority Data

Apr. 7, 2000 (CA) .................................. 2304906

(51) Int. Cl.
  *A61K 31/355* (2006.01)
  *A61K 31/375* (2006.01)
  *A61K 31/202* (2006.01)

(52) U.S. Cl. ............... 514/549; 514/560; 514/552; 514/558; 514/458; 514/474

(58) Field of Classification Search ............... 514/560, 514/549, 552, 558, 458, 474; 424/195.1
See application file for complete search history.

(56) References Cited

U.S. PATENT DOCUMENTS

| | | | | |
|---|---|---|---|---|
| 4,526,902 A | * | 7/1985 | Rubin ........................ | 514/560 |
| 4,871,768 A | * | 10/1989 | Bistrian et al. ............. | 514/547 |
| 5,015,483 A | * | 5/1991 | Haynes et al. ............... | 426/73 |
| 5,023,100 A | * | 6/1991 | Chang et al. ............... | 426/601 |
| 5,043,328 A | * | 8/1991 | Weithmann .................. | 514/78 |
| 5,102,912 A | | 4/1992 | Streber ....................... | 514/529 |
| 5,141,958 A | * | 8/1992 | Crozier-Willi et al. ...... | 514/558 |
| 5,223,285 A | * | 6/1993 | DeMichele et al. .......... | 426/72 |
| 5,434,183 A | * | 7/1995 | Larsson-Backstrom ..... | 514/549 |
| 5,502,077 A | * | 3/1996 | Breivik et al. .............. | 514/560 |
| 5,567,730 A | * | 10/1996 | Miyashita et al. .......... | 514/549 |
| 6,077,525 A | * | 6/2000 | Vanderhoek ................ | 424/442 |
| 6,160,141 A | * | 12/2000 | Seidel ........................ | 554/126 |
| 6,710,032 B1 | * | 3/2004 | Teter et al. .................. | 514/23 |

FOREIGN PATENT DOCUMENTS

| | | |
|---|---|---|
| EP | 0209066 A1 | 1/1987 |
| EP | 0955047 A2 | 11/1999 |
| JP | 60237017 A | * 11/1985 |
| JP | 62164622 | 7/1987 |
| JP | 7291862 | 7/1995 |
| WO | WO99/18956 | 4/1999 |
| WO | WO99/44585 | 9/1999 |
| WO | WO99/59562 | 11/1999 |
| WO | WO00/55318 | 9/2000 |
| WO | WO01/03688 | 1/2001 |

OTHER PUBLICATIONS

Miller et al., "Induction of Epidermal Hyperproliferation by Topical n-3 Polyunsaturated Fatty Acids on Guinea Pig Skin Linked to Decreased Levels of 13-Hydorxyoctadecadienoic Acid (13-Hode)", J Invest Dermatol, 1990, 94:353-358.*
Cho et al., "Incorporation of 13-hydroxyoctadecadienoic Fatty acid (13-Hode) into epidermal ceramides and phospholipids: phosphlipase C-catalyzed release of novel 13-HoDE-containing diacylglycerol", J Lipid Res, 1994, 35(2):255-62.*
Truitt et al, Biochimca et Biophysica Acta 1438, 1999, pp. 239-246, Antiplatelet effects of conjugated linoleic acid isomers.
Tloti et al, Thrombosis Research 62, 1991, pp. 305-317, Effect of 13-Hydroxyoctadeca-9, 11-Dienoic Acid (13-Hode) on . . . .
Buchanan et al, Wien Klin Wochenschr, 105/11, 1993, pp. 309-313 Prevention and treatment of thrombosis: Novel strategies . . . .
Bertomeu et al, Thrombosis Research 59, 1990, pp. 819-830, Selective Effects of Dietary Fats on Vascular 13-Hode . . . .
Brister et al, Recent Adv. in Prost . . . Research, 1998, pp. 275-278, Effects of Linoleic Acid and/or Marine Fish Oil . . . .
Buchanan et al, Recent Adv. in Prost . . . Research, 1998, pp. 265-269, Effects of 13-Hode and Other Momohydroxides on Integrin . . . .
Buchanan et al, in Adv. Exp. Med Biol 469, 1998, pp. 463-469, Linoleic Acid Metabolities in Health and Disease.
Buchanan et al, Wien Klin Wochenschr 111/3, 1999, pp. 81-89, A rationale for targeting antithrombotic therapy at the . . . .
Haas et al, Adv in Prost . . . Research, vol. 21, pp. 667-670, 13-Hode Synethesis in Internal Mammary Arteries and . . . .
Buchanan et al, Canadian Jour of Cardiology, vol. 16, Sep. 2000, p. 150F, 13-Hode Prevents Vascular Hyperplasia and . . . .

* cited by examiner

*Primary Examiner*—Brian Kwon
(74) *Attorney, Agent, or Firm*—Jacobson Holman PLLC

(57) ABSTRACT

This invention relates to the regulation of vascular endothelium biocompatibility and to the inhibition of vessel wall cell and other types of cell hyperplasia following vessel wall dysfunction and/or injury. More particularly, the invention relates to the dietetic and pharmaceutical preparations of 13-hydroxyoctadeca-9Z, 11E-dienoic acid (13-HODE) and its use in reducing or inhibiting vessel wall hyperlasia and restoring vessel wall biocompatibility.

7 Claims, 6 Drawing Sheets

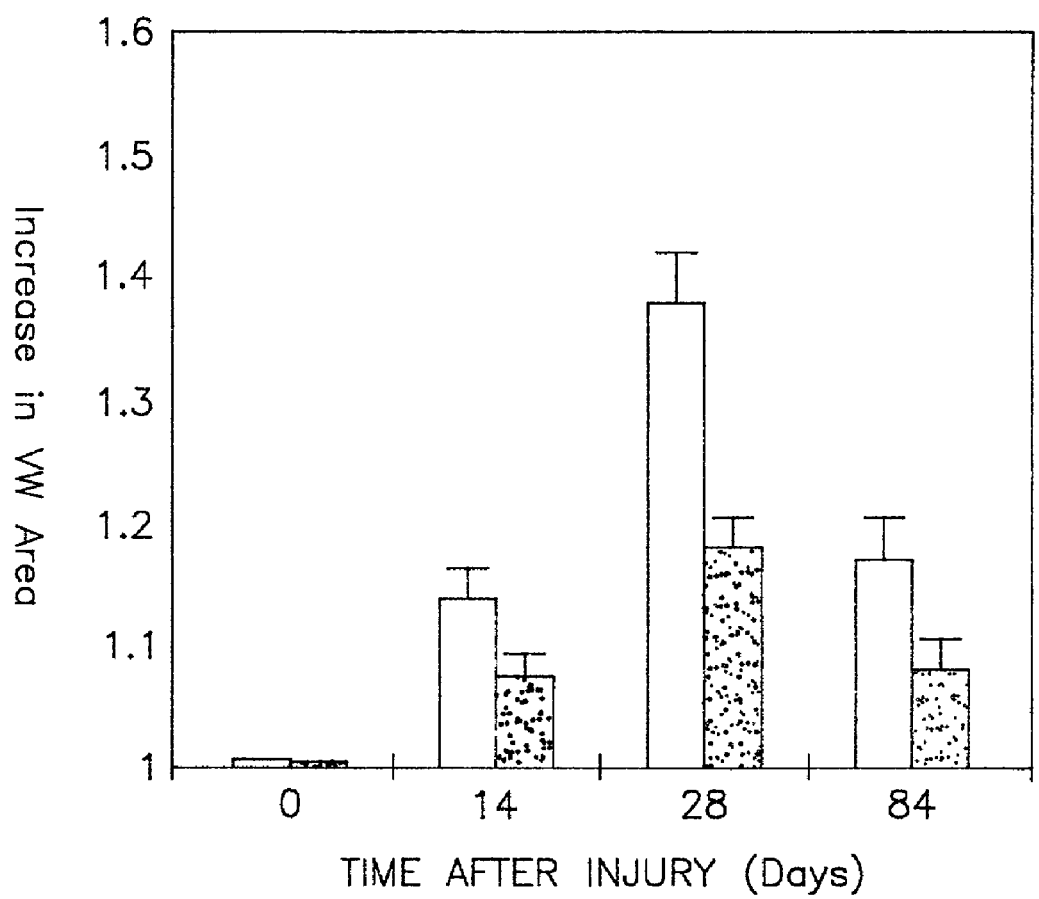

FIG. 6

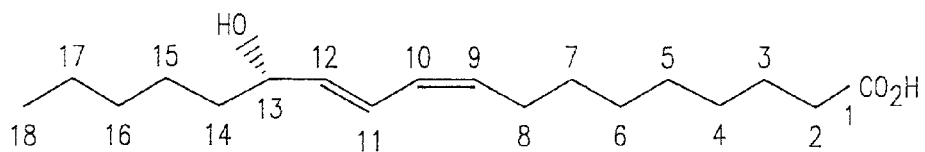

Proton nmr spectrum (270MHz; CDCl$_3$)

$\delta$(ppm) 6.5(1H, dd, $H_{11}$ $J_{11,10}$ =11Hz, $J_{11,12}$ =15.2Hz), 6.0(1H, t, $H_{10}$, $J_{10,9}$ =$J_{10,11}$ =11Hz), 5.7(1H, dd, $H_{12}$, $J_{12,11}$ =15.2Hz, $J_{12,13}$ =6.8Hz), 5.4(1H, dt, $H_9$, $J_{9,8}$ =7.7Hz, $J_{9,10}$ =10.8Hz), 4.1(1H, m, $H_{13}$), 2.4(2H, t, $H_2$, $J_{2,3}$ =7.3Hz), 2.2(2H, m, $H_8$), 1.6(4H, m, $H_3$, $H_{14}$), 1.3(14H, m, $H_{17}$, $H_{16}$, $H_{15}$, $H_7$, $H_6$, $H_5$, $H_4$) and 0.9 (3H, t, $H_{18}$, $J_{18,17}$ =6.7Hz).

Carbon-13 nmr spectrum (67.8MHz, CDCl$_3$)

$\delta$(ppm) 179.3($C_1$), 135.6($C_{12}$), 132.6($C_9$), 127.8($C_{10}$), 125.8($C_{11}$), 72.9($C_{13}$), 37.1–22.4($C_{17}$, $C_{16}$, $C_{15}$, $C_{14}$, $C_8$, $C_7$, $C_6$, $C_5$, $C_4$, $C_3$, $C_2$) and 13.9($C_{18}$).

Infrared spectrum

3500–2500cm$^{-1}$ (broad O–H stretch) and 1709cm$^{-1}$ (C=O stretch)

Ultraviolet spectrum (ethanolic solution)

$\lambda$max=232nm ($\varepsilon \equiv$ 25,000 mol$^{-1}$ dm$^3$ cm$^{-1}$)

Soluble in ethanol, dichloromethane

Insoluble in hexane, water.

USE OF 13-HODE AS A REGULATOR OF VASCULAR BIOCOMPATIBILITY AND AN INHIBITOR OF CELL HYPERPLASIA

FIELD OF THE INVENTION

This application claims the benefit of CANADA 2,304,906 filed Apr. 07, 2000.

This invention relates to the regulation of vascular endothelium biocompatibility, as well as to the inhibition of vessel wall (VW) cell and other types of cell hyperplasia following vessel wall (VW) dysfunction and/or injury. Specifically, this invention relates to dietetic and pharmaceutical preparations of 13-hydroxyoctadeca-9Z, 11E-dienoic acid (13-HODE) and its use to restore vascular endothelial cell biocompatibility, thereby rendering the vasculature less reactive to circulating blood constituents during acute pathophysiological responses and decreasing chronic hyperplasic cell responses during and/or following VW stimulation, dysfunction or injury.

BACKGROUND OF THE INVENTION

Cell cell interactions play a fundamental role in the genesis of most diseases including cardiovascular disease, cancer and metastasis, and infection and inflammation. The disadvantages and limitations of current antithrombotic therapies and the advantages of the present invention are discussed below in the context of cardiovascular disease, however these discussions are also relevant to other disease states.

Cardiovascular Disease: Treatment and Prevention—State of the Art

Cardiovascular disease is a major cause of morbidity and death in Western societies. It is exacerbated by smoking, hyperlipidemia, hypertension and diabetes. Over the last 40 years, our society has taken multiple steps to reduce cardiovascular disease such as promoting a healthier lifestyle, particularly in regard to smoking and diet. Nonetheless, each year, there are >600,000 percutaneous transluminal coronary angioplasty (PTCA) and surgically invasive procedures, e.g. coronary artery bypass grafting (CABG) in N. America alone, performed in cardiovascular disease patients to improve (cardio)vascular blood flow. While these procedures are beneficial to many patients, the benefits are finite and short-lived, and VW stenosis will reoccur. (RITA Trial Participants. 1993; Kirklin J W et al. 1989). For example, restenosis occurs in 25-30% of patients within 6 months of PTCA despite acute heparin treatment, followed by continuous aspirin (ASA) treatment±oral anticoagulants throughout the 6 month post PTCA period. Heparin is given to accelerate thrombin inhibition by antithrombin III (ATIII), thereby preventing fibrinogen cleavage to fibrin and subsequent fibrin clot formation; ASA is given to acetylate platelet cyclooxygenase, thereby inhibiting thromboxane $A_2$ ($TxA_2$) synthesis which renders platelets less reactive to prothrombotic stimuli; an oral anticoagulant, e.g. coumadin, is given to decrease the level of vitamin K-dependent procoagulants, thereby decreasing the amounts of procoagulant substrates available for thrombus formation. Thus, the current approach to treat cardiovascular disease is to impair platelet function and/or coagulation as a means to prevent (re)occurrence of heart and blood vessel disease. It does not repair the underlying defect, the latter of which if attempted, might return the patient to a normal healthier state.

The only approaches currently proposed to reverse cardiovascular disease, are the use of lipid lowering agents which decrease the risk of atheriosclerotic lesion formation, and gene therapy. The former approach also has provided some benefit, but again, it does not 'fix' the underlying problem. Gene therapy may, in fact, address the issue of repairing the underlying defect(s), but gene therapy for cardiovascular disease is still in its infancy, and not without the risk of complex side effects Libby P and Ganz P. 1997).

A treatment process, which not only corrects the underlying cause of the disease problem but also prevents its onset, is therefore needed. The present invention, which relates to the use of 13-HODE in the regulation of blood cell/VW compatibility per se, offers a mom effective approach than do current antithrombotic therapies to both treating and preventing diseases like cardiovascular disease.

Rationale for Regulating VW Biocompatability

In order to better understand the rationale for regulating VW biocompatibility and its benefits over current antithrombotic treatment practices, the rationale behind the current antithrombotic strategies and their obvious limitations is set out below. This, in turn, will highlight some insights which have led to the concept of regulating VW biocompatibility and the novel approach of using 13-HODE to treat and prevent cardiovascular disease of the present invention.

Regulating VW Biocompatibility

1. Vessel Wall Stenosis & Occlusion:

The problem of vascular stenosis and subsequent occlusion is one of the most important of all medical problems and can produce a very wide range of diseases, the best known of which are coronary, cerebral and peripheral arterial blockage. It is, of course, very difficult and perhaps impossible to study the earliest development of such arterial blockages in humans. People who feel healthy are not inclined to submit to invasive procedures, which, in turn, may detect the onset of the disease before it manifests clinical symptoms. However, it is generally accepted that the processes of restenosis after an artery has been cleared or partially cleared of the occlusive material by a procedure such as angioplasty, is likely in many aspects to be similar to the processes involved in the original development of the problem. Vascular restenosis and occlusion after angioplasty or after vessel wall injury is therefore widely used as a model of the whole series of events involved in both primary and secondary arterial occlusion.

Vascular restenosis thought to occur as a result of a combination of intimal smooth muscle cell (SMC) proliferation, SMC synthesis and secretion of extracellular matrix, and VW remodelling. (Schwartz S M et al. 1995; Strauss B H et al. 1994; Chervu A, Moore W S. 1990; Bocan T M A, Guyton J R. 1985). SMC proliferation per se, occurs in response to the mitogenic effects of thrombin generated at the time of VW injury, to platelet-derived growth factor (PDGF) secreted by platelets which adhere at the site of VW injury, and to mitogens secreted by activated endothelial cells (Bocan T M A, Guyton J R. 1985; Chen L B, Buchanan J M. 1975; Ross R. 1993; Bretschneider E et al. 1997; Fischman D L et al. 1994; Grandaliano G et al. 1998; Stouffer G A et al. 1998).

Polymorphonuclear leukocytes (PMNs) and monocytes/macrophages also invade the VW injury site, activating both coagulation and platelets, thereby augmenting the hyperplasia process (Alexander R. W. 1994; Mallory G A et al. 1939; Mehta J L et al. 1998). Moreover, invading monocytes differentiate into macrophages, ingest lipids, calcium and other blood-derived constituents, thereby forming a more complex atherosclerotic plaque (Chervu A, Moore W S.

1990; Bocan T M A, Guyton J R. 1985). Thus, there is a multiplicity of cell cell interactions, which trigger and sustain intimal hyperplasia and subsequent restenosis (Ross R. 1993; Schwartz R S. 1998; Cicala C, Cirino G. 1997).

All of these events involve the interactions of blood components with the VW, which under 'healthy conditions' occur in response to injury and infection—but do not lead to (cardio)vascular disease. However, when these blood component/VW interactions are exaggerated such as with induced SMC proliferation, platelet/fibrin thrombus formation and VW hyperplasia, (cardio)vascular disease is initiated.

2. VW Injury, Repair and Remodelling:

Recent studies debate the relative contributions of intimal VW hyperplasia per se versus VW remodelling after injury, to subsequent VW restenosis in the clinical setting. Lafont, Post, Mintz et al. argue that W remodelling associated with internal elastic lamina dilation or constriction, contributes more to restenosis after PTCA than intimal hyperplasia (Lafont A et al. 1995; Post M J et al. 1994). The results of the Benestent and STRESS studies are said to be consistent with that argument since increasing the coronary artery diameter with a stent, decreases the need for revascularization (Fischman D L et al. 1994; Grandaliano G et al. 1998). Coats et al agree since there is more SMC-derived collagen (and presumeably more SMGs) in non-stenosed VWs than in stenosed VWs (Coats W D et al. 1997; McGee M P et al. 1995.). The opposite might be expected if hyperplasia was the predominate cause for restenosis. Coats et al. suggested that the failure of our current antithrombotic therapy to inhibit restenosis as effectively as expected, is because that therapy focuses predominantly on inhibiting SMC proliferation. These conclusions, however, do not consider the heterogeneity of proliferating SMCs and their capacity to synthesise various matrices (Frid M G et al. 1997), or the fact that SMC collagen synthesis is affected by the presence (or absence) of the endothelium. Specifically, endothelial cells inhibit SMC protein synthesis, particular type III collagen (Myers P R, Tanner M A. 1998). The opposite is not true. It is also known that the extracellular matrix within a hyperplastic intima of a $1^{st}$ injury VW, is rich in elastin while the extracellular matrix within the hyperplastic intima of a $2^{nd}$ injury VW, is rich in collagen (Buchanan M R, Brister S J. 1998), (Capron L et al. 1997.). Moreover, the clinical studies cited above were performed with patients who also required a stent due to the complex nature of their lesions. The restenosis rate in those patients is >4×'s the restenosis rate in PTCA patients who do not require a stent (Antoniucci D et al. 1998). The treatment of PTCA patients who require a stent also differs significantly from the treatment of PTCA patients who do not require a stent (Antoniucci D et al. 1998). These differences are likely to affect subsequent outcome, both at the basic and the clinical end point levels. It is more likely that the relative roles of SMC hyperplasia and VW remodelling in restenosis varies depending on the type of injury and the type of the antithrombotic therapy use.

3. Blood Cell/Injured Vessel Wall Interactions:

Normally, the VW is nonthrombogenic and, therefore, biocompatable with the circulating blood. When the VW is injured, it becomes highly thrombogenic. Injured veins and arteries express tissue factor in both their media and intima. This expression increases over time after injury. Tissue factor expression is minimal in uninjured VWs (Channon K M et al. 1997). Tissue factor expression is enhanced further by PMNs and/or monocyte/macrophages, which invade the injury site. This enhancement is dependent on PMN and/or monocyle/macrophage CD18 integrin expression (Channon K M et al. 1997; McGee M P et al. 1995). VW tissue factor expression activates prothrombin, which is widely distributed throughout VW tissue rich in SMCs (McBane R D et al. 1997). Thrombin upregulates endothelial cell PDGF receptor expression, thereby facilitating SMC proliferation (Grandaliano G et al. 1998; DiCorleto P E, Bowen-Pope D F. 1983), and platelet activation. Activated platelets secrete $TxA_2$ (which is vasoconstrictive), PDGF (which is mitogenic for SMCs) and procoagulants, which exacerbate coagulation (Pakala R et al. 1997). Platelet-related factor Xa/Va activity bound to the injured VW also renders it highly thrombogenic. This latter effect persists for >96 hours (Ghigliotti G et al. 1998). Thus, the multiplicity of these events could be addressed through use of an antithrombotic therapy which targets coagulation, platelet function and inflammation, and which also targets VW thrombogenicity per se. To date, this latter approach is virtually non-existent.

4. Anticoagulant Therapy and VW Hyperplasia:

A number of studies demonstrate that heparin can inhibit experimentally-induced SMC proliferation in vitro and in vivo (Castellot J J Jr et al. 1984; Clowes A W, Clowes M M. 1986; Ferrell M et al. 1992; Hanke H et al. 1992). This suggests that heparin should prevent SMC hyperplasia and subsequent restenosis clinically. However, restenosis occurs clinically despite heparin treatment. It is now recognized that thrombin is protected from inhibition by ATIII and the acceleration of that effect by heparin when thrombin binds to fibrin or other constituents on the injured VW surface (Okwusidi J I et al. 1991; Okwusidi J I et al. 1990; Hogg P J, Jackson G M. 1989; Bar-Shavit R et al. 1989). Moreover, the surface-bound thrombin remains active, contributing to systemic hypercoagulation despite anticoagulant therapy (Ghigliotti G et al. 1998; Brister S J et al. 1993; Wells J et al. 1994; Gill J B et al. 1993). Consequently, surface-bound thrombin can activate platelets, SMC proliferation and further coagulation unchecked. There also is evidence that SMCs, which proliferate in response to repeated injury, are less sensitive to the heparin treatment than SMCs, which proliferate in response to a first injury (Capron L et al. 1997; Geary R L et al. 1995).

5. Antiplatelet Therapy and Hyperplasia

There is little evidence that antiplatelet therapy per se reduces SMC hyperplasia. Clearly, ASA is beneficial in reducing the risks of stroke, myocardial infarction and transient ischemic attacks in patients with a variety of cardiovascular diseases (Aspirin Trialists' Collaboration. 1994). However, the overall risk reduction with ASA, is only □ 25% (Aspirin Trialists' Collaboration. 1994). While this risk reduction is statistically significant, the reduction is modest at best.

Also, ASA may benefit only certain subgroup of patients (Buchanan M R, Brister S J. 1995; Grotemeyer K-H et al. 1993; Grotemeyer K H. 1991). This may be due, in part, to the wide variation in platelet responsiveness to assorted stimuli after ASA ingestion (Mueller M R et al. 1997). The effect of ASA is also finite and has little benefit after 2 years (Aspirin Trialists' Collaboration. 1994).

Alternate antiplatelet agents which block the platelet glycoprotein IIb/IIa (GPIIb/IIIa) receptor have been proposed as superior alternates to ASA. The EPILOG study demonstrated that blocking the GPIIb/IIIa receptor with c7E3 decreases acute ischemic complications in patients undergoing PTCA (The EPILOG Investigators. 1997). Similar results were obtained in the PRISM study using Aggrastat, a non-peptide GPIIb/IIIa antagonist (The Platelet Receptor Inhibition in Ischemic Syndrome Management (PRISM) Study Investigators. 1998). It also has been suggested that the short t½ (half-life) of these compounds may circumvent any bleeding side effect as compared to ASA. However, the bleeding issue still remains controversial. More importantly, like with aspirin, there is little clinical evidence to suggest that long-term hyperplasia is inhibited by these compounds.

Given recent studies, it is not surprising that platelet function inhibitors have little effect on preventing hyperplasia and restenosis. Specifically, Sirois et al made animals thrombocytopenic and then injured their arteries. Thrombocytopenia was sustained for short or long periods of time, and then their platelet counts were restored to normal levels. While the onset of VW hyperplasia was delayed in the long-term thrombocytopenic animals, the potential for SMC proliferation was not inhibited at all. Thus, medial SMC PDGR-β receptor expression was upregulated in all animals despite their being or not being thrombocytopenic. As a result, when the platelet count was restored to normal, SMC proliferation and subsequent intimal hyperplasia were initiated (Sirois M G et al. 1997). These data not only emphasise the need to regulate acute platelet/VW interactions to inhibit chronic intimal hyperplasia, but also suggest that platelet inhibition alone for any finite period of time is unlikely to have a lasting effect.

6. Limitations With the Current Antithrombotic Therapies

While all of the studies cited above, both experimental and clinical clearly indicate clinical benefits with the varied approaches to attenuate the different stages in the development of atherosclerosis, none of these approaches prevent disease onset or facilitate disease regression. Moreover, all of the therapeutic approaches mentioned above act indirectly by compromising coagulation, platelet function and/or injured vessel wall repair. As a result, all patients receiving any form of the currently recommended antithrombotic therapies, are rendered hemostatically dysfunctional, and therefore, at a significant hemorrhagic risk. Thus, there is a clear need for a better antithrombotic approach which leads to the prevention and/or reversal of vascular disease, and which achieves these effects without any adverse side effects.

7. 13-HODE VW Biocompatibility and Hyperlasia

The concept of preventing VW hyperplasia by altering VW biocompatibility has not been considered directly, except perhaps, from the perspective of reducing fat and cholesterol intake in an attempt to reduce VW lipid accumulation and fatty streak formation on the VW. Most attempts have focussed more on the isolation and recombinant synthesis and subsequent utilization of VW constituents to alter blood component properties. For example, there is both experimental and clinical data to suggest that endothelial cell-derived nitric oxide, tissue plasminogen activator and prostacyclin are useful in the treatment of patients at risk of acute thromboembolic events (Gershlick A H et al. 1994; Zerkowski H-R et al. 1993; The GUSTO Investigators. 1993). Their effects, like the antiplatelet and anticoagulant therapies, target platelet function, vessel wall calibre and thrombolysis, thereby compromising hemostasis and coagulation. Moreover, it should be noted that all of these are only produced by the VW following injury or activation, and have little effect on regulating the innate biocompatable properties of a healthy, injured or diseased VW per se.

13-HODE is produced in various cells and tissues of the body, particularly by vascular endothelial cells in healthy vessel walls and by dermal epithelial cells. 13-HODE is formed by the action of an enzyme known as 15-lipoxygenase on the dietary essential fatty acid, linoleic acid. The first step is oxidation of the linoleic acid to give 13-hydroperoxyoctadeca-9Z, 11E-dienoic acid (13-HODE). This is then reduced to 13-HODE. 13-HODE is an important signal transduction molecule which is short-lived and whose synthesis is activated by a variety of different stimuli (Buchanan M R et al. 1985; Haas T A et al. 1990; Weber E et al. 1990; Bertomeu M-C et al. 1990; Brister S J et al. 1990; Buchanan M R, Bastida E. 1988; Cho Y, Ziboh V A. 1994; Mari I. 1998; Kang L-T et al. 1999; Pongracz J, Lund J M. 1999; Friedrichs et al. 1999; C Y, Ziboh V A. 1994). Many of the effects of 13-HODE are mediated by inhibition of protein kinases (PK), particularly PKC and mitogen-activated PK (MAP kinase).

13-HODE which is an oily liquid can be incorporated in much the same way as its parent fatty acid, linoleic acid, into a range of complex molecules including phospholipids and triglycerides (Spiteller G. 1998; Fang X et al. 1999). 13-HODE which is not incorporated into complex lipids is rapidly metabolized by hydrogenation and beta-oxidation (Bronstein J C, Bull A W. 1993; Hecht, Spiteller G. 1998).

Almost all of the studies designed to investigate the effects of 13-HODE involve measuring the effects of altering endogenous 13-HODE production or by adding exogenous 13-HODE (in various forms) to cultured cells in vitro. In the past, there have been few studies, which measure the effects of 13-HODE when given orally or parenterally to animals or humans. This limitation has been due, in part, to the difficulties of making large quantities of 13-HODE and its availability to the scientific community. Consequently, the amount of 13-HODE needed for in vivo studies has been extremely expensive. Second, generally it has been believed that 13-HODE is unstable and readily metabolized, like many signal molecules. As such, it has been thought that it would be a waste of time and money to perform studies involving the oral administration of 13-HODE since none of the orally administered material would be expected to reach its target site of action.

However, there are a few studies which suggest that orally administered 13-HODE has biological relevent effects in vivo. Strews patent describes the use of 13-HODE and other related fatty acids to inhibit aromatase enzymes, which convert androgens to estrogens. The purpose of the treatment is to act on any disease, which is induced by estrogen such as breast cancer, and possibly some types of benign prostatic hyperplasia. However, it should be noted that all of the evidence provided in Streber's patent is based on data obtained in vitro. There are no experiments, which demonstrate that that invention actually works in viva. Moreover, Streber does not provide any details regarding the methods of administration or any practical details as to how the materials might be formulated (although it is stated that 'tablets or capsules or dragees' may be used). Finally, the daily dose specified ranges from 100 to 1,000 mg, preferably in the 200 to 500 mg ran. (Streber A S. Hydroxy-octadecadienoic acid for the treatment of estrogen-dependent disease. U.S. Pat. No. 5,102,912, April 1992).

The only study known to us which actually describes any experiments whereby a hydroxy derivative of linoleic acid has been administered orally outside of the experiences with the present invention discussed below, is that of Kaminakai et al (Japanese patent, #7-291862, Nov. 7, 1995). However, they only mention 13-HODE in passing. The actual hydroxy derivative of linoleic acid manufactured for patent use in their experiments, is a different fatty acid; namely, 9-hydroxy-10(E)-12(Z) octadecadienoic acid (9-HODE) which is described in the NMR spectrum shown in FIG. 2 of their patent, and which is stated in the text to be the material actually manufactured and studied in their experiments. These experiments involved the use of 9-HODE given orally to influence the action of Sarcoma 180 tumors implanted in the abdominal cavity of mice. They report an inhibitory effect on the rate of tumour growth, but the minimum effective dose required is 55 mg/kg/day.

The only 13-HODE studies which focus specifically on altering VW biocompatibility to prevent thrombogenesis have been reported by Buchanan et al. Their earlier studies demonstrate that healthy VW cells continuously turn over linoleic acid; i.e. at a time when the endothelium is non-thrombogenic or biocompatable with the circulating blood (Buchanan M R et al. 1985). Intracellular linoleic acid is metabolized to 13-HODE via the lipoxygenase pathway (Haas T A et al. 1990).

They also reported that:
i) endogenous VW 13-HODE plays an important role in regulating VW biocompatibility under both healthy and thrombogenic situations. For example, VW cell thrombogenicity varies inversely with VW 13-HODE levels in both animals and humans. Therefore, increasing endogenous levels of 13-HODE in both animals and humans results in a decrease in VW cell thrombogenicity (Weber E et al. 1990; Bertomeu M-C et al. 1990; Brister S J et al. 1990; Buchanan M R, Brister S J. 1994); and a decrease in platelet/VW interactions following injury. (Weber E et al. 1990; Bertomeu M-C et al. 1990; Buchanan M R, Brister S J. 1994); and
ii) 13-HODE down regulates the ability of the vitronectin receptor to recognise its ligands, thereby decreasing its adhesivity for vitronectin, fibronectin and fibrin(ogen) (Buchanan M R et al. 1998).

The mechanisms underlying these protective effects of 13-HODE are thought to involve inhibition of protein kinases (PK), particularly PKC and mitogen-activated PK (MAP kinase).

It is important to emphasize that in all of these studies, the aim was always to raise the level of endogenous production of 13-HODE by Undulating its endogenous synthesis or breakdown. None of these studies considered manipulating vessel wall 13-HODE levels by the exogenous administration of 13-HODE. This is clearly demonstrated by a series of experiments involving the administration of Persantine (dipyridamole) which is a phosphodiesterase inhibitor and which was thought might regulate endogenous 13-HODE metabolism.

In these experiments, it was demonstrated that an anti-thrombotic therapy which involved increasing VW 13-HODE levels, decreased SMC hyperplasia. Rabbits were treated with Persantine (1 mg/kg/day for 7 days) before a $1^{st}$ or a $2^{nd}$ VW injury, and then 4 weeks later, intimal SMC hyperplasia was measured. Persantine was given on the basis that it inhibits phosphodiesterase, thereby increasing VW cAMP levels (Weber E et al. 1990; Haas T A et al. 1990). Increasing VW cAMP increased VW linoleic-acid turnover and subsequent VW 13-MODE synthesis, which, in turn, was associated with decreased platelet/VW interactions at the time of injury (Weber E et al. 1990). The Persantine treatment inhibited SMC hyperplasia 4 weeks after VW injury. Platelet function in these animals was unchanged.

These studies are consistent with the discovery that decreasing VW thrombogenicity by increasing VW 13-HODE at the time of injury will attenuate long-term intimal hyperplasia and subsequent VW restenosis. Moreover, this approach did not compromise normal hemostasis and coagulation like the currently used clinical approaches do.

13-HODE, Anti-inflammatory Therapy and VW Hyperplasia

Inflammation has been recognized as an integral part of the thrombotic process as early as 1939 (Mallory G A et al. 1939), yet it is not considered in the rationale for our current antithrombotic therapies. However, there is convincing evidence that attenuating certain inflammatory responses provide a significant benefit. For example, monocytes/macrophages and PMNs express the integrin CD11/CD18 (ICAM), and they release cytokines when activated (Peracchia R et al. 1997; Yasukawa H et al. 1997; Turek J J et al. 1998), which, in turn, stimulate i) $\beta_3$ integrin expression in other cells such as platelets, endothelial cells and SMCs (Blanks J E et al. 1998; Golino P et al. 1997); ii) tissue factor activation (McGee M P et al. 1995); and iii) PDGF expression (Rubin P et al. 1998; Panek R L et al. 1997). Lipid fractions derived from platelets augment these responses by inducing monocyte/macrophage differentiation and growth (Ammon C et al. 1998). Macrophages interacting with the injured vessel wall, accumulate lipid, leading to the formation of a more complex atherosclerotic lesion (Ross R. 1993; Post M J et al. 1994). Blocking monocyte/macrophage ICAM expression reduces VW hyperplasia significantly (Golino P et al. 1997; Nageh M R et 1997; Natori S at al. 1997). Others have found that radiation ($^{90}$Sr/Y or $^{192}$Ir) at doses, which selectively impair monocyte/macrophage function also, decreases VW hyperplasia in both rodent and rabbit models (Rubin P et al. 1998; Panek R L et al. 1997; Williams D O. 1998; Kipshidze N et al. 1998). In a preliminary clinical study, the SCRIPPS trial using endovascular radiation, the restenosis rate in 35 patients undergoing PTCA who also required a stent was 11%, significantly less than the 37% restenosis rate seen in comparable non-irradiated controls (Williams D O. 1998). These data provide direct evidence, which suggests that altering inflammatory responses also affect intimal hyperplasia and subsequent VW restenosis.

Studies by Buchanan et al suggest that the culprit inflammatory cell is not the PMN. In fact, PMNs may attenuate vessel wall thrombogenicity by providing a source of 13-HODE at the site of blood cell/VW interactions at the time of VW injury (Buchanan M R. 1989; Buchanan M R et al. 1993). Others have argued that PMN-derived oxygen radicals promote ischemia-related damage (Shen J et al. 1996), but this has not been linked to long-term hyperplasia. PMNs also secrete, a nitric oxide-like factor, which inhibits platelet function and vasoconstriction (Cerletti C et al. 1992). Monocytes/macrophages, on the other hand, normally do not synthesize 13-HODE (Shen J et al. 1996; Shen J et al. 1995). Interestingly however, Shen et al upregulated 15-lipoxygenase in differentiated macrophages and found that 13-HODE synthesis increased. This increase was associated with decreased macrophage lipid accumulation. Fan et al. also found that macrophages enriched with linoleic and gamma linolenic acids (substrates for 13-HODE and $PGE_1$, respectively), stimulate intracellular SMC cAMP which, in turn, decreases SMC proliferation (Fan Y Y et al. 1997). Finally, 13-HODE inhibits PAF (platelet activating factor)-induced PMN and monocyte/macrophage degranulation and ICAM expression (Cerletti C et al. 1992), thereby preventing further integrin-dependent cell cell and cell ligand interactions.

Recent Studies with 13-HODE

The above data suggest that endogenous VW 13-HODE plays an important role in regulating VW biocompatibility under both healthy and thrombogenic situations, and that 13-HODE is therefore a useful antithrombotic agent. However, any progress in developing that concept has been thwarted by the lack or absence of any agent which would directly upregulate 13-HODE synthesis by VW cells, PMNs or other relevent cells. While Persantine has been a useful tool to generate preliminary data, it is a weak and reversible inhibitory of phosphodiesterase. Supplementing a diet of cardiovascular diseased patents with linoleic acid (the substrate for 13-HODE)) also has been useful to demonstrate the benefit of elevating VW 13-HODE levels. However, that approach requires the patients to ingest a daily dose of 20 grams or more of linoleic acid-rich capsules, and the treatment is not without its unwanted side effects, including an increased caloric intake.

Surprising Results

To date, researchers working in the field have concentrated on the idea of maintaining healthy endothelial cell function either by regulating the endogenous production of 13-HODE, avoiding factors which suppress its synthesis and/or providing agents containing linoleic acid which may enhance the synthesis of 13-HODE. It was thought that only trivial amounts of purified 13-HODE would reach the target site of the VW endothelium if administered orally, and would, therefore, be biologically inactive. Recently, these ideas were tested and, surprisingly, proven wrong. Specifically, it was found that orally administered 13-HODE does reach its intended targets and is biologically active. In addition, suitable vehicles in which 13-HODE can be administered orally were identified. And most amazingly, the beneficial effects of orally administered 13-HODE are achieved with unexpectedly low doses.

These and other objects and advantages of the invention will be apparent to those skilled in the art from a reading of the following description and appended claims.

SUMMARY OF THE INVENTION

This invention relates to a method of reducing or inhibiting cell and vessel wall hyperplasia and restoring vessel wall biocompatibility, comprising administering to an animal or human in need of such treatment an amount of 13-hydroxyoctadeca-9Z, 11E-dienoic acid (13-HODE) effective to reduce or inhibit vessel wall thrombogenicity wherein the compound is administered orally.

This invention also relates to the method described above wherein the pharmaceutical composition comprises 13-HODE either in its free form, or with a pharmaceutically acceptable carrier, auxiliary or excipient.

The carrier, auxiliary or excipient may be mono-, di- or triglyceride oil, corn, sunflower, safflower, cottonseed, grape seed, olive, evening primrose, borage, fish body and fish liver oils, or an ester of a fatty acid containing 16–26 carbon atoms and one or more double bonds. The estermay be ethyl-eicosapentaenoic (ethyl-EPA), oleic, linoleic, alpha-linoleic, stearidonic, gamma-linolenic, dihomogammalinolenic, arachidonic, docosapentaenoic or docosahexaenoic (DHA).

This invention also includes a pharmaceutical composition comprising 13-HODE and a fat-soluble antioxidant, such as, ascorbyl palmitate, tocopherols, and ascorbic acid in the presence of lecithin.

Furthermore, this invention relates to a pharmaceutical composition comprising 13-HODE and an additive selected from the group consisting of aggregants, disaggregants, osmotic pressure regulating salts, buffers, sweeteners, and coloring agents.

The pharmaceutical composition or 13-HODE of this invention may be administered in the form of a dietetic composition, or as a formulation selected from the group consisting of tablets, dragees, capsules, granules, suppositories, solutions, suspensions and lyophilized compositions. A pharmaceutical composition as described above wherein the daily dose of 13-HODE is equal to or less than 100 mg is also part of this invention.

The invention further relates to a pharmaceutical composition comprising 13-HODE and an omega-3 fatty acid (such as EPA, DHA, or any a derivative of EPA or DHA, such as ethyl-EPA or ethyl-DHA).

The invention includes a method of correcting the inhibition of endogenous 13-HODE synthesis by omega-3 fatty acids by incorporating 13-HODE into formulations of omega-3 fatty acids.

The method and the pharmaceutical composition of 13-HODE of this invention may be used to treat cardiovascular or cerebrovascular disease, inflammatory or autoimmune disease, infection with bacteria, viruses, fungi, or protozoa, respiratory disease, gastrointestinal disease, renal or urinary tract disease, skin disease, neurological or psychiatric disease, disease of the reproductive system, diabetes, syndrome X or any complication of diabetes, diseases associated with overactive protein kinases, and diseases associated with endothelial dysfunction.

The method and the pharmaceutical composition of 13-HODE of this invention may also be used to treat and/or prevent cancer or the metastatic spread of cancer.

Other and further advantages and features of the invention will be apparent to those skilled in the art from the following detailed description of the invention taken in conjunction with the accompanying drawings.

BRIEF DESCRIPTION OF THE DRAWINGS

In the accompanying drawings:

FIG. 3 illustrates the effect of 13-HODE, suspended in corn oil, on increase of vessel wall area of injured vessel walls from rabbits treated orally with 0 or 1000 µg/kg/day for 7 days.

FIG. 6 illustrates the properties of 13-hydroxyoctadeca-9Z, 11E-dienoic acid (13-HODE).

DETAILED DESCRIPTION OF THE INVENTION AND PREFERRED EMBODIMENTS

Figure 1:
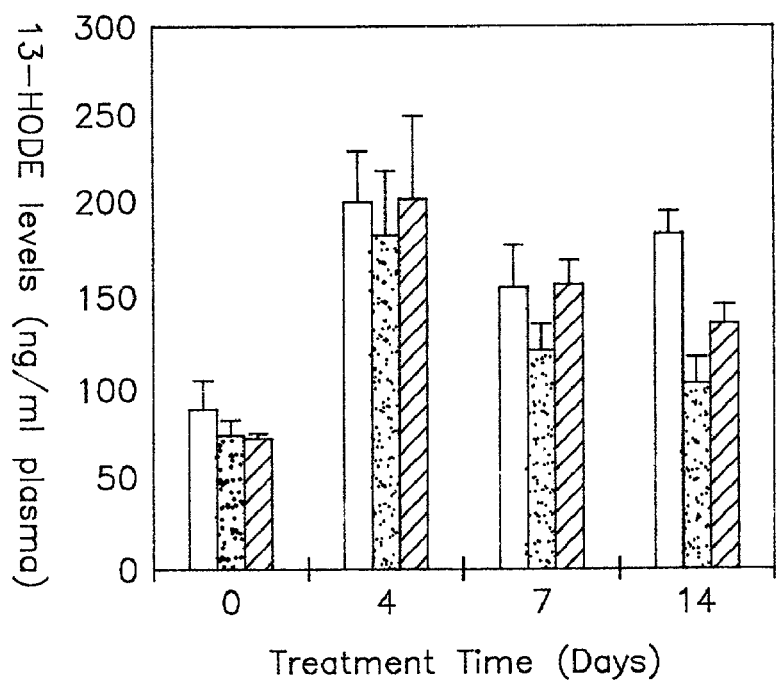
FIG. 1 & FIG. 1A illustrates the cell free plasma 13-HODE levels in rabbits treated orally with 13-HODE (suspended in corn oil, upper; or EPA, lower) at 100 to 1000 µg/kg/day on days 1 to 7.
Figure 1A:
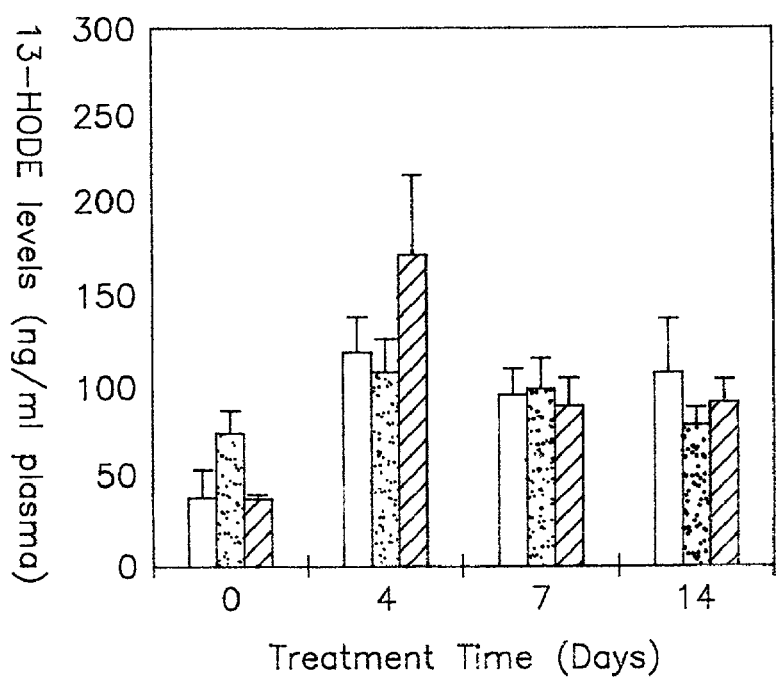

The present invention demonstrates a method for reducing or inhibiting vessel wall hyperplasis and restoring vessel wall biocompatability in a mammal or human in need of such treatment, by administering an amount of 13-hydroxy-octadeca-9Z, 11E-dienoic acid (13-HODE) effective to reduce or inhibit vessel wall thrombogenicity.

The present invention also specifically demonstrates the beneficial effects of exogenously administered 13-HODE in animals and humans of vascular response to VW injury, including the prevention and treatment of vessel wall hyperplasia, as well as the facilitation of vessel wall disease regression.

As discussed earlier, 13-HODE is one of the factors, which regulates vessel wall biocompatibility, thereby attenuating untoward blood component/vessel wall interactions. It may do this in several ways, one of which probably is to reduce the expression and activation of the vitronectin receptor. In recent years, it has been found that abnormalities of vessel wall biocompatibility are associated with a remarkable number of illnesses, including infections, cardiovascular problems of many types, as well as to problems relating to inflammation, fibrosis and loss of normal metabolic control (Vallance et al. 1997), and tumour cell metastasis. In all of these illnesses, vascular endothelial cells are activated, leading to the loss of the normal vascular permeability barrier, expression of leukocyte adhesion molecules, change in VW surface thromboreactivity, the production of a wide range of cytokines and the upregulation of HLA antigens (Hunt B J, Jurd K M.). A wide range of illnesses may be caused or exacerbated by endothelial cell activation and damage.

The present invention through the regulation of endothelial function in a favourable direction by 13-HODE, will therefore have a desirable effect in a wide variety of diseases encompassing almost every aspect of medicine. Of particular interest is the fact that the administration of exogenous 13-HODE in this invention is able to compensate for any suppression of endogenous 13-HODE synthesis which can occur as a result of administration of omega-3 fatty acids such as alpha-linoleic acid, docoapentaenoic acid and particularly EPA and docosahexaenoic acid (DHA) (Miller and Ziboh, as above). EPA and DHA have many desirable actions but sometimes the clinical results of administering EPA and DHA are less favourable than expected, as in the case with attempts to prevent reocclusion after angioplasty (Cairns et al, as above). The co-administration of 13-HODE with EPA or DHA or other omega-3 fatty acids is therefore of particular value.

The composition according to the present invention can be formulated for administration orally, Thus the composition may be in the form of tablets, capsules, suspensions, emulsions and solutions.

Formulations for oral use include tablets, which contain the active ingredient in admixture with nontoxic pharmaceutically acceptable excipients. The excipients may be, for example, inert diluents, such as calcium carbonate, sodium chloride, lactose, calcium phosphate or sodium phosphate; granulating and disintegrating agents, for example, potato starch or alginic acid; binding agents, for example, starch, gelatin, or acacia; and lubricating agents, for example, magnesium stearate, stearic acid or talc. Other pharmaceutically acceptable excipients can be colorants, flavoring agents, plasticizers, humectants etc. The tablets may be uncoated or they may coated by known techniques, optionally to delay disintegration and absorption in the gastrointestinal tract and thereby provide a sustained action over a longer period. For example, a time delay material such as glyceryl momostearate or glyceryl distearate may be employed.

Formulations for oral use may also be presented as chewing tablets, or as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil. Powders, dispersible powders or granules suitable for preparation of an aqueous suspension by addition of water are also convenient dosage forms of the present invention. Formulation as a suspension provide the active ingredient in admixture with a dispersing or wetting agent, suspending agent and one or more preservatives. Suitable dispersion or wetting agents are, for example, naturally-occurring phosphatides, as e.g. lecithin, or condensation products of ethylene oxide with e.g. a fatty acid, a long chain aliphatic alcohol or a partial ester derived from fatty acids and a hexitol or hexitol anhydrides, for example, polyoxyethylene stearate, polyoxyethylene sorbitol monooleate, polyoxyethylene sorbitan monooleate etc. Suitable suspending agents are, for example, sodium carboxymethylcellulose, methylcellulose, sodium alginate etc.

The pharmaceutically acceptable carriers or excipients may include emulsifying agents, antioxidants, buffering agents, preservatives, humectants, penetration enhancers, chelating agents, gelforming agents, ointment bases, perfumes and skin protective agents. Examples of emulsifying agents are naturally occurring gums, e.g. gum acacia or gum tragacanth, naturally occurring phosphatides, e.g. soybean lecithin and sorbitan monooleate derivatives. Examples of antioxidants are butylated hydroxy anisole (BHA), ascorbic acid and derivatives thereof, tocopherol and derivatives thereof and cysteine. Examples of preservative are parabens and benzalkonium chloride. Examples of humectants are glycerin, propylene glycol, sorbitol and urea. Examples of penetration enhancers are propylene glycol, DMSO, triethanoiamine, N,N-dimethylacetamide, N,N-dimethylformamide, 2-pyrrolidone and derivatives thereof, tetrahydrofurfuryl alcohol and Azone.RTM. Examples of chelating agents are sodium EDTA, citric acid and phosphoric acid. Examples of gel forming agents are Carbopol, cellulose derivatives, bentonit, alginates, gelatin and PVP. Examples of ointment bases are beeswax, paraffin, cetyl palmitate, vegetable oil, sorbitan esters of fatty acids (Span), polyethyleneglycols and condensation products between sorbitan esters of fatty acids and ethylene oxide, e.g. polyoxyethylene sorbitan monooleate (Tween). The formulation and preparation of the above-mentioned compositions is well known to those skilled in the art of pharmaceutical formulation. Specific formulation can be found in "Remington's Pharmaceutical Sciences".

Dietetic compositions of the present invention may be made up in the form of emulsions, for example, sauces, mayonnaise or margarine.

One embodiment of the invention relates to the administration of a pharmaceutical composition, in conjunction with a pharmaceutically acceptable carrier, for the therapeutic effects, which are discussed below.

In a preferred embodiment of the invention, the pharmaceutical composition of 13-HODE is administered orally, and comprises a combination product containing 13-HODE in combination with a carrier from the group consisting of corn, sunflower, safflower, cottonseed, grapeseed, olive, evening primrose, borage, fish body, fish liver oils, ethyl-eicosapentaenoic, oleic, linoleic, alpha-linolenic, stearidonic, gamma-linolenic, dihomogammalinolenic, arachidonic, docosapentaenoic or docosahexaenoic (DHA).

In another preferred embodiment, the pharmaceutical composition of the present invention comprises a combination product containing 13-HODE in combination with corn oil in a ratio between about 1:3 to about 1:100. For example, 50 mg of 13-HODE can be mixed with 450 mg corn oil.

In another embodiment, the pharmaceutical composition of the present invention comprises a combination product containing 13-HODE in combination with an ester carrier in a ratio of about 1:3 to about 1:100.

In yet another embodiment, the pharmaceutical composition of the present invention comprises a combination product containing 13-HODE in combination with an ethyl ester of a 16–26 carbon fatty acid with one or more double bonds, such as ethyl-oleate, ethyl-linolate, ethyl-EPA or ethyl-DHA.

The pharmaceutical composition in a further embodiment of the present invention comprises 13-HODE is incorporated into the Sn1 or Sn2 positions of an appropriate phospholipid prior to mixing with a carrier.

In another preferred embodiment of the invention, the pharmaceutical composition comprises 13-HODE and omega-3 fatty acids, like EPA, DHA, derivatives of EPA and DHA, ethyl-EPA and ethyl-DHA.

The compositions are useful when administered in methods of medical treatment or prophylaxis of a disease, disorder or abnormal physical state associated with abnormalities of vessel wall biocompatibility, including cardiovascular or cerebrovascular, inflammatory or auto-immune, respiratory, gastrointestinal, renal, skin, neurological and psychiatric diseases and cancers. Examples of diseases, which can be treated or prevented by administering the pharmaceutical composition of the present invention include both Type I, Type II and the precursor Type II diabetes, syndrome X (Cosentino F, Lucher T F. 1998; Steinberg A D. 1997), many types of inflammatory disorders including rheumatoid arthritis and osteoarthritis and autoimmune diseases (Perretti M. 1997), infections with bacteria and protozoa like malaria and sleeping sickness, and fungi which can generate endotoxins (Gerrity et al. 1976), sickle cell disease and related haemoglobins disorders (Lubin B H. 1997), kidney disease (Clausen et al. 1999), inflammatory bowel disease (Binion D G et al. 1998) pregnancy hypertension and pre-eclampsia (Endresen M J R et al. 1998), normal aging (Hashimoto M et al. 1999), dementias (ladecola C et al. 1999), retinal ischemia and age-related macular degeneration (Gidday J M, Zhu Y. 1998; Wada M et al. 1999), cancer and especially cancer metastasis and angiogenesis (Pinedo H M et al. 1998; Shureigi I et al. 1999; Baron Ja et al. 1998; Hazelton D et al. 1999), all types of cardiovascular diseases (Kanani P M et al. 1999), hyperlipidemias and atherosclerosis of all types (Lefer D J, Granger D N. 1999; Mombouli J-V. 1999; Blann A D. 1999; Brown B G, Zhao X -Q. 1998; Freedman J E, Loscalzo J. 1997; Abe Y. 1998), transplantation (Labarrere C A et al. 1997), pulmonary hypertension (Higenbottom T W, Laude E A. 1998), hypertension and heart failure (Boulanger C M. 1999), and in Raynaud's syndrome (Edwards C M et al. 1999). In addition, smoking can be treated with the present invention as endothelial function also is impaired by smoking (Motoyama T et al., 1997) in normal people who have a high fat meal (Plotnick G D et al., 1997), and in apparently healthy people who had a low birth weight or who are at risk of cardiac disease (Goodfellow J et al.) Endothelial function is impaired in fit young adults of low birth weight. (Ridker P M et al., 1998) Plasma concentrations of soluble intercellular adhesion molecule 1 and risks of future myocardial infarction in apparently healthy men. (*Lancet*, 1998).

Dosages to be administered depend on individual patient condition, indication of the drug, physical and chemical stability of the drug, toxicity of the desired effect and the chosen route of administration (Robert Rakel, ed., Conn's Current Therapy (1995, W. B. Saunders Company, USA)).

The following Examples are presented as specific illustrations of the present invention. It should be understood, however, that the invention is not limited to the specific details set forth in the Examples.

EXAMPLE 1

Identifying the Appropriate Vehicle for 13-HODE

13-HODE is a colourless or very pale yellow oily liquid. Within the body 13-HODE can be metabolized as described earlier or transferred intact between various possible complex lipids including triglycerides, diaglycerides (diacylglycerols), monoglycerides, cholesterol esters and phospholipids of many different types. As a pharmaceutical, 13-HODE may be used as is, or be dissolved in various carriers, or be incorporated into glyceride, ester, phospholipid or other molecules with any appropriate carrier. Glycerides, esters of propane diol, ethyl esters and phospholipids to which 13-HODE is co-valently bound and any other molecules or vehicles which can release 13-HODE in a biologically active form within the body all lie within this invention.

A real problem is presented by the fact that active daily doses of 13-HODE are in the 50 to 1,000 μg/kg/day range. The lower end of this range, 100 μg/kg/day, was shown to be highly biologically active in rabbits. That translates into a 7 mg/day dose for a 70 kg person. Since doses for humans are often considerably lower than doses for animals because of a weight/body surface area scaling, a daily dose of as little as 5 mg or less is really possible. Formulating an oily liquid is such small doses is a problem. It could be absorbed into tabletting materials and tabletted and coated, or microencapsulated by methods well known to those skilled in the art. However, the most convenient and preferred dosage forms of 13-HODE, and the ones in which it was found to be stable without degradation, was to dissolve the 13-HODE into a triglyceride oil carrier or an ester. It was found that corn oil is a particularly useful diluent, and that 13-HODE can be readily and conveniently mixed with corn oil in a ratio, for example, from 1:3 to 1:100. Other triglyceride oils such as vegetable oil, including sunflower, safflower, soy, evening primrose, borage, coconut or palm oil, or cottonseed, rapeseed, olive, fish body or fish liver oils may all be used for this purpose. Particularly useful esters for this purpose are esters of fatty acids with 16–26 carbon atoms and one or more double bonds in the chain. Ethyl ester of EPA was found to be particularly appropriate, but equivalent esters of fatty acids such as oleic, linoleic, alpha-linoleic, stearidonic, gamma-linoleic, dihomogammalinoleic, arachidonic, docosapentaenoic and DHA are all examples of esters which could be useful to carry the 13-HODE.

The preparations can then be further processed to give a final dosage form. The oils can be ingested directly, or appropriate antioxidants or flavours can be added, or they can be converted into palatable, flavoured emulsions by the use of emulsifying agents or flavouring well known to those skilled in the art. A particularly valuable dosage form is a soft gelatin or bonded hard gelatin capsule, or a similar capsule made with agar or other appropriate materials.

At present, the only readily available supplies of 13-HODE are in very expensive mg quantities for use as laboratory reagents. The properties of the pure material are shown in FIG. 6. Larger quantities can now be prepared using soybean lipoxygenase or an enzyme of similar specificity. This enzyme metabolizes linoleic acid to 13-HODE. The reaction can be carried out in an appropriate vessel filled with a cooling and stirring system and pH, oxygen (dissolved oxygen content, DOC), and temperature probes. The reaction is first charged with 0.1 M borate buffer which is then chilled to below 100° C. The buffer is then purged with oxygen until the DOC reaches 100%. Soybean lipoxygenase is then added at the rate of about 2500 U/liter and the mixture is stirred and regularly purged with oxygen to keep the DOC at 100%. Octa-deca-9Z, 12Z-dienoic acid, dissolved 1/1 in ethanol is then added at a rate of about 10 g/liter. The reaction is then pressurized with an overblanket of oxygen, and vigorously stirred. The reaction is allowed to proceed, and monitored at 15 minute intervals by ultraviolet analysis and thin layer chromatography analysis to confirm the conversion of the linoleic acid to 13-HODE.

On completion of the reaction, the vessel is flushed with nitrogen and reduced by adding sodium borochydride at the rate of about 3.3 g/liter. On completion of the reduction process, the mixture is acidified to pH 6 with citric acid. Reverse phase silica (OD53) is then added and stirred and the mixture is allowed to continue to stir overnight under nitrogen at room temperature. The silica absorbs the 13-HODE, which is then recovered by filtering the silica, washing it with water, and then eluting out the product by multiple washing with acetonitrile. The solvent is then washed off and the crude oil is purified by column chromatography with diethyl ester and methylene chloride to yield pure 13-HODE as a viscous pale yellow oily substance. This material can then be formulated as discussed above.

In some of the experiments conducted, corn oil was used because it had previously been found that suspending linoleic acid in corn oil facilitated its selective uptake by the VW (Bertomeu M-C et al. 1990). In other experiments, marine fish oil was used (specifically marine menhaden or 97% pure ethyl eicosapentaenoic (ethyl-EPA)) since marine fish oils such as tuna, sardine or other oils also are suitable to maintain 13-HODE stability. Ethyl-EPA was of great interest therapeutically because EPA has many desirable actions other than on the VW endothelium such as the inhibition of platelet aggregation, the lowering of triglyceride levels and the attenuation of inflammation. However, it also can inhibit the formation of endogenous 13-HODE, which might be a possible negative effect (Miller C C, Ziboh, V A. 1990; Gimenez-Amau A et al. 1997).

This inhibitory effect of EPA may help explain why the expected desirable cardiovascular effects of EPA have not been realized in practice. For example, a continuous course of EPA treatment failed to reduce restenosis after occluded coronary arteries had been opened by angioplasty (Caims J A et al. 1996).

Materials and Methods:

New Zealand white rabbits (half males/half females; 2.5–2.9 kg) were used throughout. Rabbits were treated with 100, 400 or 1000 µg/kg/day of purified 13-HODE suspended in corn oil or ethyl-eicosapentaenoic acid (EPA), or with an equivolume of either suspending vehicle (total volume 1 ml) for 7 days. Serial blood samples were collected before, during and after treatment to assess the levels of 13-HODE in plasma. On day 7, the treatments were stopped. At that time, the rabbits were anaesthetised with a combination of Atravet, Ketamine, Vetrepham and glycopyrolate, given subcutaneously. Both carotid arteries of anaesthetised rabbits were isolated between 2 temporary ligatures, first by applying the proximal ligature, then allowing the blood to drain from the segment, and then applying the distal ligature. A 24-gauge angiocath attached to tubing filled with sterile saline and connected to a pressure manometer, was inserted into the isolated segment. Then the segment was filled with the saline to a pressure of 600 mm Hg which was maintained for 5 minutes. The pressure was relieved, and the angiocath and ligatures were removed, thereby allowing for blood flow restoration. Cessation of bleeding from the needle puncture site was achieved within 3 minutes without any manual manipulation. The incisions were sutured closed with 000 proline. The rabbits were injected intramuscularly with Temgesic to minimize any pain and with 12.5 mg Baytril as an antibiotic, and then allowed to recover. This injury procedure results in endothelial denudation and the exposure of a thrombogenic surface within 1 hour of restoration of blood flow, followed by SMC proliferation and intimal hyperplasia, which plateaus at □ 4 weeks and which is sustained for ≧12 weeks (Buchanan M R, Brister S J: 1998: Buchanan M R et al. 1999).

Two, four or twelve weeks later, the rabbits were re-anaesthetised and their injured carotid arteries were again isolated. Segments of injured and uninjured carotid artery were harvested and processed histologically to assess VW hyperplasia. Other VW segments and blood samples were collected and processed for VW and plasma 13-HODE levels.

Results

Plasma 13-HODE Levels: There was a three-fold increase in the plasma 13-HODE levels after 7 days of treatment with 100 µg/kg/day of 13-HODE suspended in corn oil (FIG. 1, upper panel). Increasing the 13-HODE dose to 1,000 µg/kg/day had no further effect. The plasma 13-HODE levels returned back to almost control levels within 14 to 21 days. Similar results were seen when the 13-HODE was suspended in ethyl-EPA (FIG. 1, lower panel), although the absolute levels of plasma 13-HODE were lower in all treatment levels tested. Notwithstanding, there were no significant differences in the dose-related increases in plasma 13-HODE levels between the two suspending vehicle treatment groups.

Figure 2:
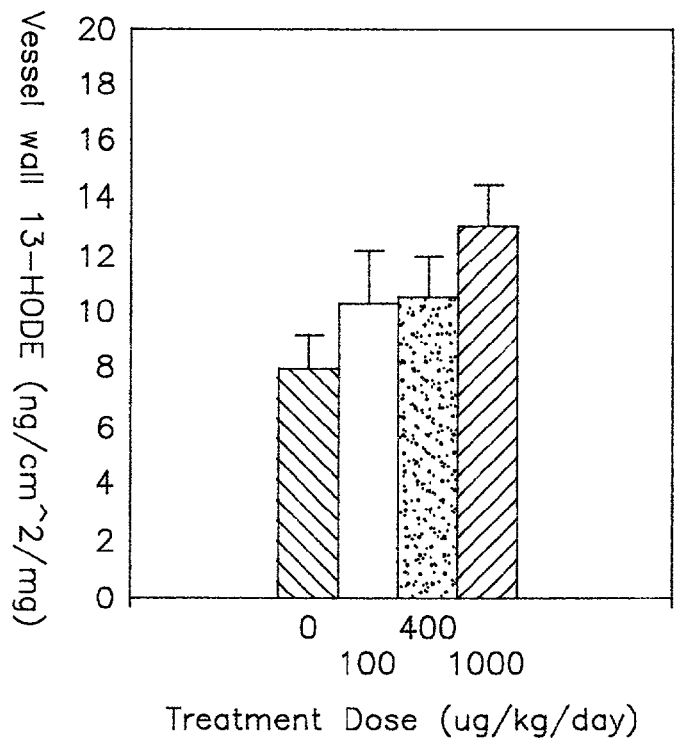
FIG. 2 & FIG. 2A illustrates 13-HODE levels in vessel walls obtained from rabbits treated orally with 0 to 100 µg/kg/day for 7 days. 13-HODE was suspended in corn oil (upper) or EPA (lower) and given on days 1 to 7.
Figure 2A:
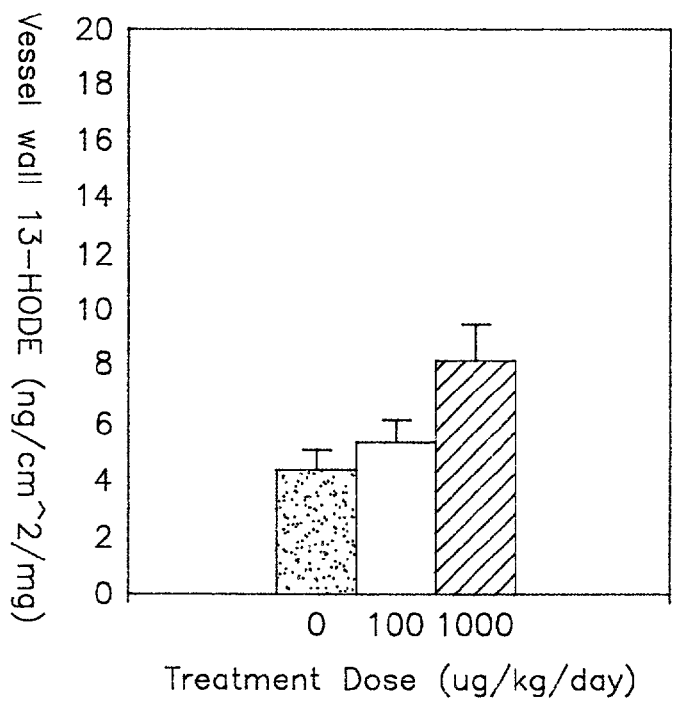

VW 13-HODE Levels: There also was a dose-related increase in VW wall 13-HODE levels in the rabbits treated with 13-HODE suspended in corn oil and measured 28 days after stopping the treatment (FIG. 2, upper panel). These data indicated the VW 13-HODE levels remain elevated despite stopping the treatment. This may be due to the 13-HODE being incorporated into complex lipids as demonstrated by Fang et al (1999).

Similar results were seen when the 13-HODE was suspended in ethyl-EPA (FIG. 2, lower panel), but again, the absolute levels of VW 13-HODE were somewhat lower at all treatment levels tested. Since the VW 13-HODE levels were of course a measurement of both endogenous- and exogenously-derived 13-HODE, it is possible that the lower VW 13-HODE levels seen in the ethyl-EPA treated group reflect a suppression of endogenous 13-HODE synthesis as described by Miller and Ziboh (1990).

Figure 4:
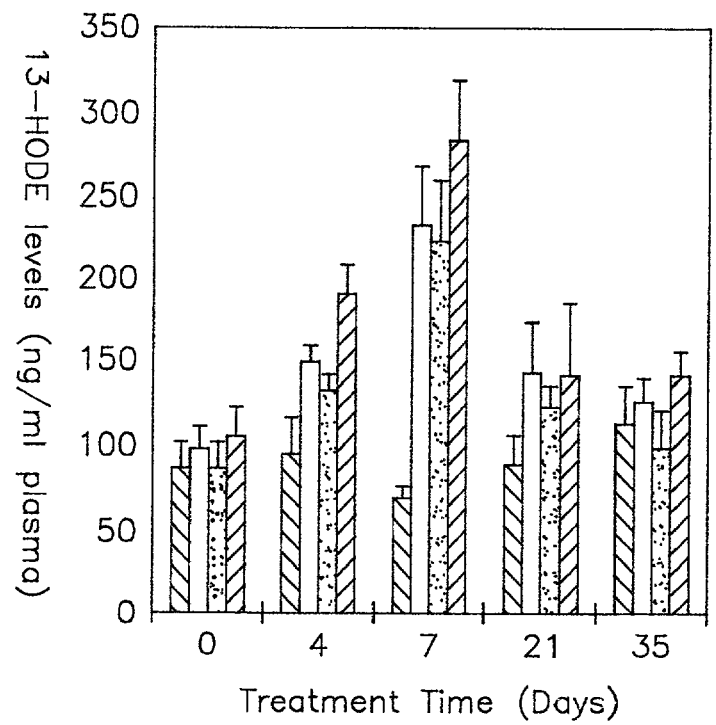
FIG. 4 & FIG. 4A illustrates cell free plasma 13-HODE levels in rabbits treated orally with 13-HODE (suspended in corn oil upper; or EPA, lower) at 100 to 1000 µg/kg/day on days 1 to 7.
Figure 4A:
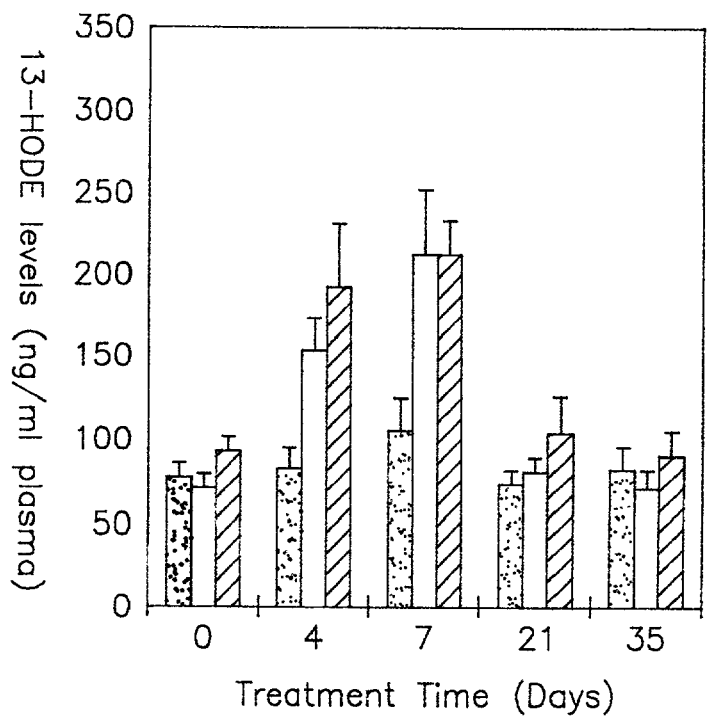

Biological Effects: In the initial studies with the purified 13-HODE, the marked increases in VW 13-HODE were associated with a significant decrease in intimal hyperplasia measured 2 and 4 weeks after injury. Thus, intimal hyperplasia in rabbits treated with 1,000 μg/kg/day of 13-HODE, was 8 and 16% at 2 and 4 weeks respectively, compared to 18 and 38% hyperplasia seen at 2 and 4 weeks, respectively in the placebo treated rabbits, $p<0.002$ (FIG. 3). Moreover, the intimal hyperplasia regressed in the 13-HODE treated animals such that intimal hyperplasia was barely detectable at 12 weeks, >3%, $p<0.01$. This is the first direct evidence demonstrating that purified 13-HODE inhibits VW intimal hyperplasia. It was interesting to note that the 13-HODE level in the cell-free plasmas of those animals not only was elevated significantly within 3 days of treatment, but remained elevated for 4 weeks despite our stopping the 13-HODE treatment after 7 days (FIG. 4). These latter data suggest that orally administered 13-HODE is well absorbed, has a long half life, and can be monitored relatively easily in a clinical setting. These latter data also suggested to us that a markedly lower dose of 13-HODE could be as effective in preventing VW intimal hyperplasia.

EXAMPLE 2

Figure 5:
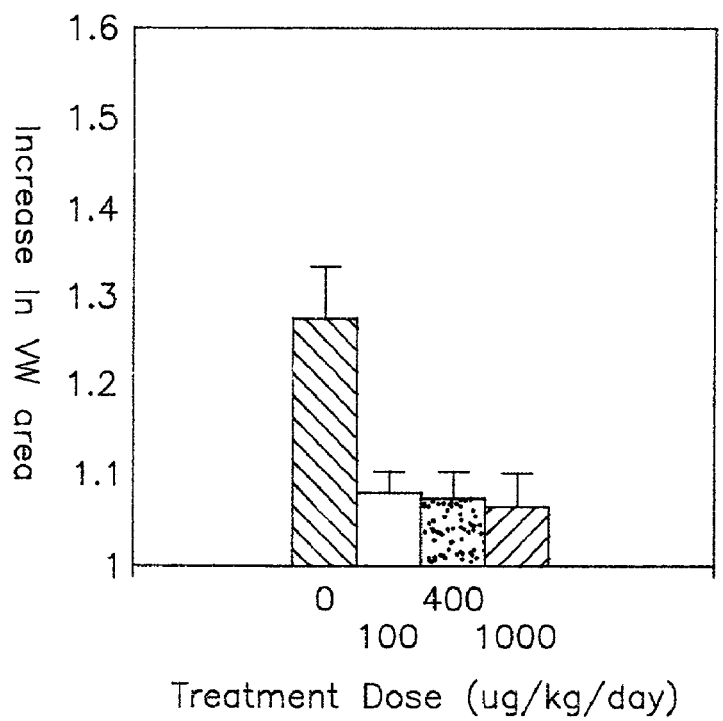
FIG. 5 & FIG. 5A illustrates effect of 13-HODE, suspended in corn oil (upper) or EPA (lower), on increase of vessel wall area of injured vessel walls from rabbits treated orally with 0 to 1000 µg/kg/day for 7 days.
Figure 5A:
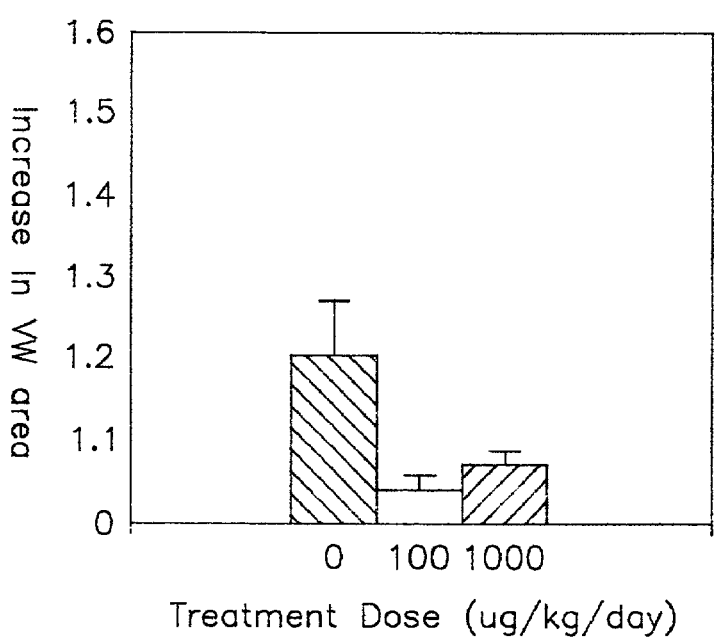

Rabbits were administered a 7 day course of 100 μg/kg/day of 13-HODE suspended in either corn oil or ethyl-EPA, significantly inhibited intimal VW hyperplasia, $p<0.001$ (FIG. 5). The rises in VW 13-HODE and the inhibition of VW hyperplasia were considerably greater than could be achieved by attempting to raise 13-HODE levels indirectly, for example by giving its precursor linoleic acid or by giving Persantine. For comparison, when patients ingest 3.2 gm of linoleic acid daily (20 capsules) for 30 days, VW 13-HODE levels only increases 2-fold (Buchanan M R, Brister S J. 1994), and when rabbits were treated with Persantine in a dose comparable to that used clinically, VW 13-HODE only increased 30 to 50% (Weber E et al. 1990). Platelet/injured VW interactions were decreased >2-fold in both cases.

These recent data demonstrate that the effect; i.e. inhibition of intimal hyperplasia, is achieved with an amazingly low dose of 13-HODE, and because hyperplasia regresses. No other current antithrombotic treatment has this capability. This effect is achieved without impairing platelet function and coagulation, as based on earlier studies (Weber E et al. 1990; Bertomeu M-C et al. 1990; Brister et al. 1990), and the observation that there was no detectable hemorrhagic defect in any of the experimental animals.

Experimental Conclusions: The following conclusions can be made from these experiments:
1) 13-HODE prevents VW hyperplasia effective when administered orally since the 13-HODE will reach the vascular tissue and other tissues in concentrations, which are biologically, active and which restore VW biocompatibility.
2) The doses of 13-HODE, which are biologically active, are surprisingly low.
3) Triglyceride and ester oils are appropriate vehicles for the 13-HODE.
4) The biological effects of 13-HODE on the vessel wall are highly desirable.

These include both the prevention and treatment of vessel wall hyperplasia, as well as the facilitation of vessel wall disease regression.

EXAMPLE 3

13-HODE is used in a ratio of between 1:3 and 1:100 or even up to 1:1000 with triglyceride oil, particularly corn oil. For example, 50 mg of 13-HODE could be mixed with 450 mg corn oil in a soft gelatin or bonded hard gelatin capsule, or 5 mg could be mixed with 100 mg of evening primrose oil or any other appropriate oil in similar types of capsules.

EXAMPLE 4

Compositions as in Example 3 are used, but in which the oil is for direct administration as a liquid and is flavoured in an appropriate way, for example with lemon.

EXAMPLE 5

Compositions as in Example 3 are used, but in which the oil is mixed with water to form a 5 to 40% oil in water emulsion, using an appropriate emulsifier and appropriate flavourings.

EXAMPLE 6

Compositions as in Examples 3–5 are used, but in which the oil is mixed with an ester, particularly an ethyl ester of a 16–18 carbon fatty acid with one or more double bonds. Ethyl oleate, ethyl-linolate, ethyl-EPA and ethyl-DHA are examples of appropriate carriers for 13-HODE.

EXAMPLE 7

As in Examples 3–6 but in which the 13-HODE is incorporated itself into a mono-, di- or tri-glyceride prior to mixing with the carrier.

EXAMPLE 8

As in Examples 3–6, but in which the 13-HODE is incorporated itself into the Sn1 or Sn2 positions of an appropriate phospholipid prior to mixing with the carrier.

EXAMPLE 9

As in Examples 3–6, but in which the 13-HODE is incorporated into any other appropriate carrier molecule which with allow the 13-HODE to be delivered to target sites where 13-HODE is biologically active, such as the vascular endothelium.

Although preferred embodiments of the invention have been described herein, it will be understood by those skilled in the art that variations may be made thereto without departing from the spirit of the invention or the scope of the appended claims.

REFERENCES

Abe Y. Soluble cell adhesion molecules in hypertriglyceridemia and potential significance on monocyte adhesion. *Arterioscler Thromb Vasc Biol* 18: 723–731, 1998

Alexander R W. Inflammation and coronary artery disease. *N Engl J Med* 331: 468–469, 1994

Antoniucci D et al. Restenosis after coronary stenting in current clinical practice. *Am Heart J* 135:510–518, 1998

Aspirin Trialists' Collaboration. Collaborative overview of randomised trials of antiplatelet therapy. II. Maintenance of vascular graft or arterial patency by antiplatelet therapy. *Br Med J* 308: 159–168, 1994

Bar-Shavit R, Eldor A. Vlodavsky I. Binding of thrombin to subendothelial extracellular matrix. *J Clin Invest* 84: 1098–1104, 1989

Baron Ja et al. Venous thromboembolism and cancer. *Lancet* 351: 1077–1080, 1998

Bertomeu M-C et al. Selective effects of dietary fats on vascular 13-HODE synthesis and platelet/vessel wall interactions. *Thromb Res* 59: 819–830, 1990

Binion D G et al. Acquired increases in leucocyte binding by intestinal; microvascular endothelium in inflammatory bowel disease. *Lancet* 352: 1742–1746, 1998

Bocan T M A, Guyton J R. Human aortic fibrolipid lesions: progenitor lesions for fibrous plaques, exhibiting early formation of the cholesterol-rich core. *Am J Pathol* 120: 193–198, 1985

Boulanger C M. Secondary endothelial dysfunction: hypertension and heart failure. *J Mol Cellular Cardiol* 31: 39–49, 1999

Bretschneider E et al. Thrombin but not thrombin receptor activating peptide is mitogenic for coronary artery smooth muscle cells. *Thromb Res* 87 (5):493–497, 1997

Breugnot C, et al S12340: a potent inhibitor of the oxidative modification of low-density lipoprotein in vitro and in vivo in WHHL rabbits. *J Pharmacol Exp Ther* 269; 515–520, 1994.

Brister S J et al. Thrombin generation during cardiac surgery. Is heparin the ideal anticoagulant? *Thromb Haemost* 70: 259–263, 1993

Brister S J et at. 13-HODE synthesis in internal mammary arteries and saphenous veins: Implications in cardiovascular surgery. *Adv Prost Thromb Leuko Res* 21: 667–670, 1990 in cardiovascular surgery. *Adv Prost Thromb Leuko Res* 21: 667–670, 1990

Blann A D. Endothelial cell damage and the development or progression of atherosclerosis. *Clin Sci* 97: 119–121, 1999

Brown B G, Zhao X-Q. Importance of endothelial function in mediating the benefits of lipid-lowering therapy. *Am J Cardiol* 82: 49T–52T, 1998

Buchanan M R, Bastida E. Endothelium and underlying membrane reactivity with platelets, leukocytes and tumor cells: regulation by the lipoxygenase-derived fatty acid metabolites, 13-HODE and HETE's. *Med Hypothesis* 27: 317–325, 1988

Buchanan M R, Brister S J. Increasing vessel wall (V) 13-HODE metabolism with dietary fatty acid supplements in patients undergoing cardiac surgery decreases VW reactivity to platelets. *Can J Cardiol* 10 (Suppl C): 67C, 1994

Buchanan M R, Brister S J. inhibition of chronic vessel wall (re)stenosis with acute thrombin inhibition: Relative effects of heparin and dermatan sulphate. *Thromb Res* 91:157–167, 1998

Buchanan M R, Brister S J. Individual variation in the effects of ASA on platelet function: Implications for the use of ASA clinically. *Can. J Cardiol* 11: 317–321, 1995

Buchanan M R et al. 13-Hydroxy-octadecadienoic acid is the vessel wall chemorepellant factor, LOX. *J Biol Chem* 260:16056–16059, 1985

Buchanan M R et al. Regulation of endothelial cell/and platelet/receptor-ligand binding by the 12- and 15-lipoxygenase monohydroxides, 12-, 15-HETE and 13-HODE. *Prost Leuko Essential Fatty Acids* 58: 339–346, 1998

Buchanan M R et al. Evidence for a conformational change of surface-bound thrombin that promotes vessel wall thrombogenicity: Selective and sustained inhibition by intimatan but not by heparin. *Thromb Haemost* 81 (suppl): 1309, 1999

Buchanan Mr et al on behalf of the BRAT investigators. Results of the BRAT study A pilot study investigating the possible significance of ASA nonresponsiveness on the benefits and risks of ASA on thrombosis in patients undergoing coronary artery bypass surgery. *Can. J Cardiol* 16 (11): 1385–1390, 2000.

Capron L et al. Repeated balloon injury of rat aorta: a model of neointima with attenuated inhibition by heparin. *Arterioscler Thromb Vasc Biol* 17:1649–1656, 1997

Castellot J J Jr et al. Structural determinants of the capacity of heparin to inhibit the proliferation of vascular smooth muscle cells. *J Cell Physiol* 58: 315–320, 1984

Channon K M et al. Modulation of tissue factor protein expression in experimental venous bypass grafts. *Arterioscler Thromb Vasc Biol* 17; 1313–1319, 1997

Chen L B, Buchanan J M. Mitogenic activity of blood components. 1. Thrombin and prothrombin. *Proc Natl Acad Sci U.S.A.* 72:131–135, 1975

Chervu A, Moore W S. An overview of intimal hyperplasia. *Surg* 171: 433–447, 1990

Cho Y, Ziboh V A. 13-hydroxyoctadecadienoic acid reverses epidermal hyperproliferation via selective inhibition of protein kinase C-beta activity. *Biochem Biophys Res Comm* 201: 257–265, 1994

Cho Y, Ziboh V A. Incorporation of 13-HODE into epidermal ceramides and phospholipids: phospholipase C-catalyzed release of 13-HODE-containing diaglycerol. *J Lipid Res* 35: 255–262, 1994

Cicala C, Cirino G. Linkage between inflammation and coagulation: an update on the molecular basis of the crosstalk. *Life Sciences* 62 (20): 1817–1824, 1997

Clausen et al. Endothelial haemostatic factors are associated with progression of urinary albumin excretion in clinically health subjects. *Clin Sci* 97: 37–43, 1999

Clowes A W, Clowes M M. Kinetics of cellular proliferation after arterial injury: heparin inhibits rat smooth muscle mitogenesis and migration *Circ Res* 58: 839–845, 1986

Coats W D et al. Collagen content is significantly lower in restenotic versus nonrestenotic vessels after balloon angioplasty in the atherosclerotic rabbit model. *Circ* 95:1293–1300, 1997

Cosentino F, Lucher T F. Endothelial dysfunction in diabetes mellitus. *J Cardiovasc Pharmacol* 32 (suppl 3): 554 561, 1998

DiCorleto P E, Bowen-Pope D F. Cultured endothelial cells produce a platelet-derived growth factor-life protein. *Proc Nat/Acad Sci U.S.A.* 80:1919–1923, 1983

Edwards C M et al. Cardiovascular responses evoked by mild cool stimuli in primary Raynaud's disease: the rote of endothelin. *Clin Sci* 96: 577–588, 1999

Endresen M J R et al. Serum from pre-eclampsia women induces vascular adhesion molecule-1 expression on human endothelial cells in vitro. *Am J Obst Gynaecol* 179: 665–670, 1998

Fang X et al. 13-HODE incorporation and conversion to novel products by endothelial cells. *J Lipid Res* 40: 699–707, 1999

Ferrell M et al. A dilemma for the 1990's: Choosing appropriate experimental animal models for the prevention of restenosis. *Circ* 85: 1630–1631, 1992

Fischman D L et al. A randomized comparison of coronary-stent placement and balloon angioplasty in the treatment of coronary artery disease. *N Engl J Med* 331:496–501, 1994

Freedman J E, Loscalzo J. Endothelial dysfunction and atherothrombotic occlusive disease. *Drugs* 54 (suppl 3): 41–50, 1997

Frid M G et al. Smooth muscle cell heterogeneity in pulmonary and systemic vessels. *Arterioscler Thromb Vasc Biol* 17:1203–1209, 1997

Friedrichs et al. 13-HPODE and 13-HODE modulate cytokine-induced expression of endothelial cell adhesion molecules differently. *BioFactors* 9: 61–72, 1999

Geary R L et al. Failure of heparin to inhibit intimal hyperplasia in injured baboon arteries: the role of heparin-sensitive and insensitive pathways in the stimulation of smooth muscle cell migration and proliferation. *Circ* 91: 2972–2981, 1995

Gershlick A H et al. Failure of epoprostenol (prostacyclin, $PGI_2$) to inhibit platelet aggregation and to prevent restenosis after coronary angioplasty: results of a randomized placebo controlled trial. *Br Heart J* 71: 7–12, 1994

Ghigliotti G et al. Prolonged activation of prothrombin on the vascular wall after arterial injury. *Arterioscler Thromb Vasc Biol* 18:250–257, 1998

Gerrity et al. Endothel-induced vascular endothelial injury and repair. *Exp Mol Path* 24:59–69, 1976

Gidday J M, Zhu Y. Endothelium-dependent changes in retinal blood flow following ischemia. *Curr Eye Res* 17: 798–807, 1998

Gill J B et al. Thrombin generation post PTCA following cessation of heparin infusion. *Can J Cardiol* 9(E): 84E, 1993

Goodfellow J et al. Endothelial function is impaired in fit young adults of low birth weight. *Cardiovasc Res* 40: 600–606, 1998

Grandaliano G et al. Thrombin regulates PDGF expression in bovine glomerular endothelial cells. *J Am Soc Nephrol* 9: 583–589, 1998

Grotemeyer K-H et al. Two year follow up of aspirin responders and non-responders. A pilot study including 180 post stroke patients. *Thromb Res* 71: 397–403, 1993

Grotemeyer K H. Effects of acetyisalicylic acid in stroke patients: Evidence of nonresponders in a subpopulation of treated patients. *Thromb Res* 63: 587–593, 1991

Haas T A et at. Cyclic AMP regulation of endothelial cell triglyceride turnover, 13-hydroxyoctadecadienoic acid (13-HODE) synthesis and endothelial cell thrombogenicity. *Biochim Biophys Acta* 1031: 174–178, 1990

Hanke H et al. inhibition of cellular proliferation after experimental balloon angioplasty by low-molecular-weight heparin. *Circ* 85:1548–1556, 1992

Hashimoto M et al. Effect of aging on plasma membrane fluidity of rat aortic endothelial cells. *Exp Gerontol.* 34:687–698, 1999

Hazelton D et at. Vascular endothelial growth factor levels in ovarian cyst fluid correlate with malignancy. *Clin Cancer Res* 5: 823–829, 1999

Higenbottom T N, Laude E A. Endothelial dysfunction providing the basis for the treatment of pulmonary hypertension. *Chest* 114: 725–795, 1998

Hogg P J, Jackson C M. Fibrin monomer protects thrombin from inactivation by heparin-antithrombin III: Implications for heparin efficacy. *Proc Natl Acad Sci U.S.A.* 86: 619–623, 1989

Hunt B J, Jurd K M. Endothelial cell activation: a central pathophysiological process. *Br Med J* 316: 1328–1329

Ladecola C et al. SOD1 resolves cerebral endothelia dysfunction in mice overexpressing amyloid precursor protein. *Nature Neuroscience* 2: 157–161, 1999

Kanani P M et al. Role of oxidant stress in endothelial dysfunction produced by experimental hyperhomocysteinemia in humans. *Circ* 100:1161–1168, 1999

Kang L-T et al. Novel membrane target proteind for lipoxygenase-derived mono (5) hydroxy fatty acids. *Biochim Biophys Acta* 1438: 388–398, 1999

Labarrere C A et al. Endothelial activation of coronary disease in transplanted hearts. *JAMA* 278: 1169–1175, 1997

Lafont A et al. Restenosis after experimental angioplasty: intimal, medial and adventitial changes associated with constrictive remodeling. *Circ* 76:996–1002, 1995

Lancet 351: 88–92, 1998

Lefer D J, Granger D N. Monocyte rolling in early atherogenesis. *Circ Res* 84: 1353–1355, 1999

Libby P, Ganz P. Restenosis revisited—new targets, new therapies. *N Engl J Med* 337(6):418–419, 1997.

Lubin B H. Sickle cell disease and the endothelium. *New Eng J Med* 337: 1623–1625, 1997

Mari I. Upregulation of nuclear PKC and MAPkinase during hyperproliferation of guinea-pig epidermis: modulation of 13-HODE. *Cell Signalling* 10: 143–149, 1998

Mallory G A et al. The speed of healing of myocardial infarction: a study of the pathologic anatomy in 72 patients. *Am Heart J* 18:647–671, 1939

McGee M P et al. Specific regulation of procoagulant activity on monocytes. *J Biol Chem* 270 (44):26109–226115, 1995

Mehta J L et al. interactive role of infection, inflammation and traditional risk factors in atherosclerosis and coronary artery disease. *J Am Coll Cardiol* 31:1217–1225, 1998

McBane R D et al. Tissue prothrombin: universal distribution in smooth muscle. *Arterioscler Thromb Vasc Biol* 17:2430–2436, 1997

McGee M P et al. Specific regulation of procoagulant activity on monocytes. *J Biol Chem* 270 (44): 26109–226115, 1995

Miller C C, Ziboh, V A. induction of epideral hyperproliferation by topical n-3 polyunsaturated fatty acids on guinea pig skin linked to decreased levels of 13-hydroxy-octadeca-dienoic acid (13-HODE). *J Invest Dermatol* 94: 353–358, 1990

Mombouli J -V. Endothelial dysfunction: from physiology to therapy. *J Mol Cellular Cardiol* 31: 61–74, 1999

Motoyama T et al. Endothelial-dependent vasodilation in the brachial artery is impaired in smokers. *Am J Physiol* 273: H1644–50, 1997

Mueller M R et al. Variable platelet response to low-dose ASA and the risk of limb deterioration in patients submitted to peripheral arterial angioplasty. *Thromb Haemost* 78:1003–1007, 1997

Myers P R, Tanner M A. Vascular endothelial cell regulation of extracellular matrix collagen: role of nitric oxide. *Arterioscler Thromb Vasc Biol* 18:717–722, 1998

Okwusidi J I et al. Fibrin moderates the catalytic action of heparin but not that of dermatan sulfate on thrombin inhibition in human plasma. *J Lab Clin Med* 117: 359–364, 1991

Okwusidi J I et al. In vivo catalysis of thrombin inhibition by antithrombin III and heparin co-factor II and anti-thrombotic effect: Differential effects of dermatan sulfate and unfractionated heparin. *Thromb Haemorrh Dis* 2: 17–23, 1990

Pakala R et al. Effect of serotonin, thromboxane $A_2$, and specific receptor antagonists on vascular smooth muscle cell proliferation. *Circ* 96:2280–2286, 1997

Perretti M. Endogenous mediators that inhibit the leukocyte endothelium interaction. *TIPS* 18: 418–425, 1997

Pinedo H M et al. Involvement of platelets in tumour angiogenesis? *Lancet* 352: 1775–1777, 1998

Plotnick G D et al. Effect of antioxidant vitamins on the transient impairment of endothelium-dependent brachial artery vasoactivity following a single high-fat meal. *JAMA* 278:1682–1686, 1997)

Pongracz J, Lund J M A. The lipoxygenase product 13-HODE is a selective inhibitor of classical PKC isoenzymes. *Biochem Biophys Res Comm* 256: 269–272B, 1999

Post M J et al. The relative importance of arterial remodelling compared with intimal hyperplasia in lumen renarrowing after balloon angioplasty: a study in the normal rabbit and in the hypercholesterolemic Yucatan micropig. *Circ* 89:2816–2821, 1994

Ridker P M et al. Plasma concentrations of soluble intercellular adhesion molecule 1 and risks of future myocardial infarction in apparently healthy men. *Lancet* 351: 88–92, 1998).

Ridker P M et al., *Cardiovasc Res* 40: 600–606, 1998

Robert Rakel, ed., Conn's Current Therapy (1995, W. B. Saunders Company, U.S.A.)

Ross R. The pathogenesis of atherosclerosis: a perspective for the 1990's. *Nature* 362:801–809, 1993

Schwartz R S. Pathophysiology of restenosis: interaction of thrombosis, hyperplasia, and/or remodeling. *Am J Cardiol* 81 (7A): 14E–17E, 1998

Schwartz S M et al. The intima. Soil for atherosclerosis and restenosis. *Circ Res* 77: 445–465, 1995

Shureigi I et al. Decreased 13-HODE levels and 15-lipoxygenase-1 expression in human colon cancers. *Carcinogenesis* 20:1985–1995, 1999

Sirois M G et al. Rat arterial wall retains myointimal hyperplastic potential long after arterial injury. *Circ* 96:1291–1298, 1997

Steinberg A D. Endothelial function, insulin sensitivity and hypertension. *Circ* 96: 725–726, 1997

Stouffer G A et al. $\beta_3$ integrins are upregulated after vascular injury and modulate thrombospondin- and thrombin-induced proliferation of cultured smooth muscle cells. *Circ* 97:907–915, 1998)

Strauss B H et al. Extracellular matrix remodelling after balloon angioplasty in a rabbit model of restenosis. *Circ Res* 75: 650–658, 1994

The EPILOG Investigators. Platelet glycoprotein IIb/IIIa receptor blockade and low-dose heparin during percutaneous coronary revascularization. *N Engl J Med* 336: 1689–1696, 1997

The GUSTO Investigators. An international randomized trial comparing four thrombolytic strategies for acute myocardial infarction. *N Engl J Med* 329: 673–682, 1993

The Platelet Receptor inhibition in ischemic Syndrome Management (PRISM) Study Investigators. A comparison of aspirin plus tirofiban with aspirin plus heparin for unstable angina. *N Engl J Med* 338:1498–1505, 1998

The randomized intervention treatment of angina (RITA) trial. *Lancet* 341: 573–580, 1993; Kirklin J W et al. Summary of a consensus concerning death and ischemic events after coronary artery bypass grafting. *Circ* 79 (Suppl 1): 181–191, 1989

Vallance et al. infection, inflammation and infarction: does acute endothelial dysfunction provide a link. *Lancet* 349: 1391–1392, 1997

Wada M et al. Expression of vascular endothelial growth factor and its receptor mRNA in experimental choroidal neovascularisation. *Curr Eye Res* 18: 203–213, 1999

Weber E et al. Relationship between vessel wall 13-HODE synthesis and vessel wall thrombogenicity following injury. Influence of salicylate and dipyridamole treatment. *Thromb Res* 57: 383–392, 1990

Wells J et al. Thrombin generation in patients undergoing carotid endarterectomy: implications in acute vessel wall closure and antithrombotic therapy. *Thromb Res* 75:419–426, 1994

Zerkowski H -R et al. Endothelial damage of the venous graft in CABG: influence of solutions used for storage and rinsing on endothelial function. *Eur J Cardio-Thoracic Surg* 7: 376–382, 1993

The invention claimed is:

1. A method of reducing the inhibition of endogenous 13-hydroxyoctadeca-9Z, 11E-dienoic acid (13-HODE) synthesis which occurs when omega-3 fatty acids are orally administered to a subject, the method comprising orally administering to the subject an effective amount of an omega-3 fatty acids formulation consisting essentially of 13-HODE in its free form and at least one omega-3 fatty acid selected from the group consisting of ethyl-eicosapentaenoic acid and ethyl-docosahexaenoic acid comprising 13-HODE.

2. An oral pharmaceutical composition cosisting esentially of 13-hydroxyoctadeca-9Z, 11E-dienoic acid (13-HODE) in its free form, at least one omega-3 fatty acid selected from the group consisting of ethyl-eicosapentaenoic acid and ethyl-docosahexaenoic acid and a pharmaceutically acceptable excipient, for use in increasing the endogenous levels of 13-HODE in vessel wall in a subject.

3. The oral pharmaceutical composition of claim 2 wherein a daily dose of 13-HODE is equal to or less than 100 mg.

4. The oral pharmaceutical composition of claim 2, wherein the composition is administered in the form selected from the group consisting of tablets, dragees, capsules, granules, solutions, suspensions and lyophilized compositions.

5. The oral pharmaceutical composition of claim 2 wherein the pharmaceutically acceptable excipient is the composition further comprises an additive selected from the group consisting of aggregants, disaggregants, osmotic pressure regulating salts, buffers, sweeteners, and coloring agents.

6. A method of increasing the endogenous levels of vessel wall 13-HODE in a subject comprising administering an oral pharmaceutical composition to the subject in need thereof, wherein the oral pharmaceutical consisting essentially of 13-HODE in its free form and at least one omega-3 fatty acid selected from the group consisting of ethyl-eicosapentaenoic acid, ethyldocosahexaenoic acid and combination thereof.

7. An oral pharmaceutical composition consisting essentially of 13-hydroxyoctadeca-9Z, 11E-dienoic acid (13-HODE) in its free form and at least one omega-3 fatty acid selected from the group consisting of ethyl-eicosapentaenoic acid and ethyl-docosahexaenoic acid.

* * * * *